(12) United States Patent
Nakajima et al.

(10) Patent No.: US 6,258,964 B1
(45) Date of Patent: Jul. 10, 2001

(54) METHOD FOR EXTRACTING FAT-SOLUBLE COMPONENTS FROM MICROBIAL CELLS

(75) Inventors: Toshiaki Nakajima; Akihiro Kondo, both of Tokyo (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 09/445,440

(22) PCT Filed: Jun. 10, 1998

(86) PCT No.: PCT/JP98/02560

§ 371 Date: Dec. 28, 1999

§ 102(e) Date: Dec. 28, 1999

(87) PCT Pub. No.: WO98/56882

PCT Pub. Date: Dec. 17, 1998

(30) Foreign Application Priority Data

Jun. 11, 1997 (JP) .................................................. 9-167902

(51) Int. Cl.$^7$ ...................................................... C07C 1/00
(52) U.S. Cl. .............................. 554/12; 426/425; 435/134
(58) Field of Search .............................. 554/12; 426/425; 435/134

(56) References Cited

U.S. PATENT DOCUMENTS 4,816,278 * 3/1989 Sasamoto et al. .................. 426/513

FOREIGN PATENT DOCUMENTS

56/037280 * 8/1981 (JP) .
61/031496 * 2/1986 (JP) .
61/173767 * 8/1986 (JP) .
61/227790 * 10/1986 (JP) .

* cited by examiner

Primary Examiner—Deborah D. Carr
(74) Attorney, Agent, or Firm—Oblon, Spivak, McClelland, Maier & Neustadt, P.C.

(57) ABSTRACT

A method of extracting liposoluble components contained in microbial cells, including the steps of drying microbial cells containing liposoluble components, descructing and molding the resultant dry microbial cells by use of an extruder, particularly a twin screw extruder, and extracting the contained liposoluble component by use of an organic solvent. According to the present method, liposoluble components contained in cells can be extracted and recovered with enhanced efficiency, within short time, and with safety.

3 Claims, 1 Drawing Sheet

METHOD FOR EXTRACTING FAT-SOLUBLE COMPONENTS FROM MICROBIAL CELLS

This application is a 371 of PCT/JP98/02560 filed Jun. 10, 1998.

BACKGROUND OF THE INVENTION

1. Field of the Invention:

The present invention relates to a method of extracting liposoluble components contained in microbial cells, and more particularly to a method of extracting and recovering, in a highly efficient and safe manner, liposoluble components contained in microbial cells.

2. Description of the Related Art:

Microorganisms such as filamentous fungi, yeast, and algae have ability to produce lipids. Therefore, there have been practiced a variety of methods to extract lipids from microbial cells endowed with lipid-producing ability.

Lipid is generally accumulated in microbial cells, and there are known such methods that extract lipid directly from microbial cells or by descructing cell walls mechanically or by means of enzymes.

There has been known a method of extracting a liposoluble material in the following way: microbial cells having the ability to produce oils and fats are suspended in ethanol and then destructed, and the suspension is subsequently subjected to filtration and centrifugation so as to separate ethanol. An extraction solvent is added to suspend the contents, which are then subjected to destruction for extraction (as described in, e.g., Japanese Patent Application Laid-Open (kokai) Nos. 61-170397, 61-227790, 62-44170, and 62-179598).

Of these methods, the invention disclosed in Japanese Patent Application Laid-Open (kokai) No. 61-170397 relates to a multistep extraction method, in which each step requires use of a different kind of solvent such as an alcoholic solvent or a hydrocarbon solvent. Moreover, each step must involve means for separating an organic solvent from the cells. Therefore, the method has the drawback of intricate procedure.

In addition, all of the above-mentioned methods require quite a long time to recover a sufficient amount of oils and fats, and therefore, efficient extraction cannot be performed.

Further, since cells are destructed in an organic solvent, which entails the risk of fire, the method raises the problem of safety. If fire extinguishing equipment is to be installed to overcome such disadvantages, enormous cost is required, making the method uneconomical.

In order to solve these problems, there has been proposed a method in which cells dispersed in water are subjected to mechanical destruction and then brought to dryness, followed by introduction into a column, to thereby extract oils and fats by use of a solvent (Japanese Patent Application Laid-Open (kokai) No. 5-17796).

According to this method, the extraction ratio is high, and liposoluble components contained in microbial cells can be extracted and recovered in a safe manner. However, it has a drawback; finely divided fine powder particles clog the extraction column, thereby requiring prolonged time for extraction.

SUMMARY OF THE INVENTION

In order to solve these problems associated with conventional methods, the inventors of the present invention have carried out earnest studies and have found that liposoluble components contained in microbial cells can be extracted and recovered in a remarkably efficient manner and in a short time in the following way: dried microbial cells containing liposoluble components are subjected to destruction and molding by use of an extruder, particularly a twin screw extruder, and then the contained liposoluble component is extracted by use of a solvent. The present invention was accomplished based on this finding.

Accordingly, the present invention provides a method of extracting liposoluble components contained in liposoluble-component-containing microbial cells, characterized in that dried microbial cells containing liposoluble components are subjected to destruction and molding by use of an extruder, particularly a twin screw extruder, and then the contained liposoluble component is extracted by use of an organic solvent.

PREFERRED EMBODIMENTS OF THE INVENTION

Figure 1:
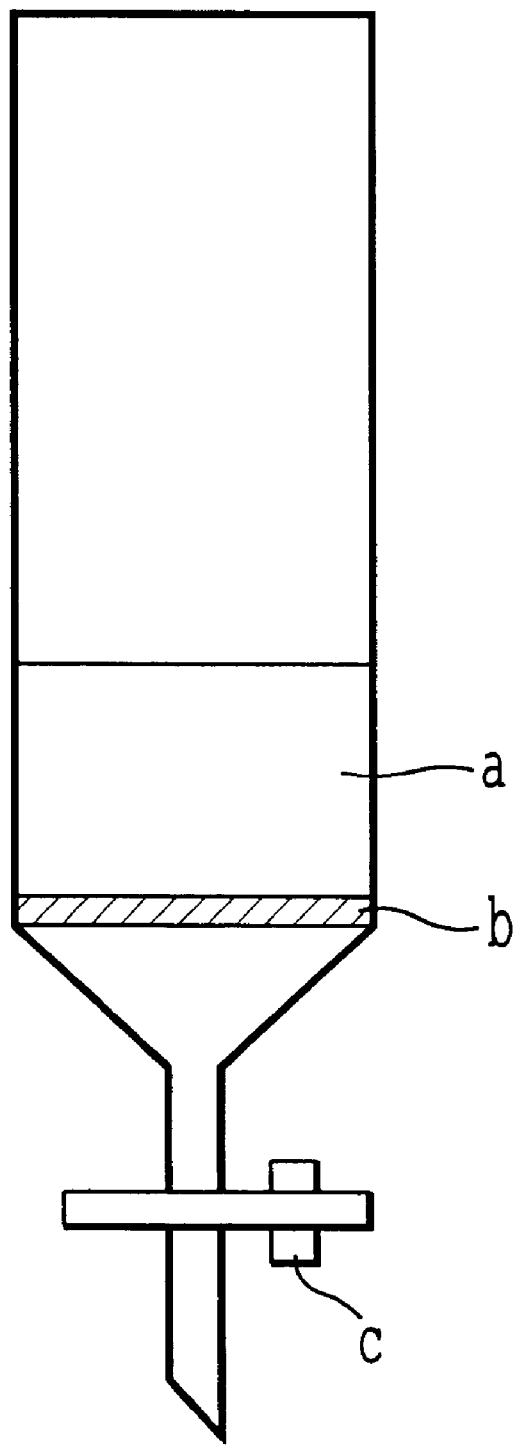
FIG. 1 is an illustration of the column used in Examples.

Liposoluble components to be extracted in the present invention refer to substances which are slightly soluble in water, soluble in an organic solvent, and present in the living body. Examples of such components include 1) simple lipids such as neutral lipids (e.g. triglycerides), waxes, glycerides, liposoluble colorants, sterols, and esters of vitamins; 2) complex lipids such as phospholipids and glycolipids; and 3) fatty acids, higher alcohols, and sterols which are considered to be precursors or metabolites of 1) and 2) above, carotenoids and squalenes which are considered to be hydrocarbons, and derived lipids comprising liposoluble vitamins.

Microbial cells containing liposoluble components used in the present invention are obtained by culturing, in a customary manner, microorganisms having ability to produce liposoluble components.

Examples of microorganisms having ability to produce liposoluble components include filamentous fungi, algae, yeast, and bacteria.

Examples of microorganisms having ability to produce a liposoluble material containing γ-linolenic acid include microorganisms that belong to the genus Mortierella, the genus Mucor, and the genus Rhizopus.

Examples of microorganisms having ability to produce a liposoluble material containing dihomoγ-linolenic acid or arachidonic acid include microorganisms that belong to the genus Mortierella and the genus Conidiobolus.

Examples of microorganisms having ability to produce a liposoluble material containing linoleic acid include microorganisms that belong to the genus Yarrowia.

Examples of microorganisms having ability to produce a liposoluble material containing docosahexaenoic acid include microorganisms that belong to the genus Crypthecodinium and the genus Schizochytrium.

More specifically, examples of microorganisms that belong to the genus Mortierella include *Mortierella isabellina* IFO 7824, *Mortierella ramaniana var. angrispora* IFO 8187, *Mortierella elongata* IFO 8570, *Mortierella exigua* IFO 8571, *Mortierella phygrophila* IFO 5941, and *Mortierella alpina* IFO 8568, IFO 32281, ATCC 8979, ATCC 16266, ATCC 32221, ATCC 32222, ATCC 32223, ATCC 36965, ATCC 42430, CBS 250.53, CBS 343.66, CBS 527.72, CBS 529.72, CBS 608.70, and CBS 754.68.

Examples of microorganisms that belong to the genus Mucor include *Mucor circinelloides* HUT 1121 (deposited with Fermentation Research Institute: FERM BP-3883), and *Mucor javanicus* HUT 1162 (strain deposited at Fermentation Research Institute: FERM BP-3884).

Examples of microorganisms that belong to the genus Ryizopus include *Ryizopus oryzae* IFO 5418.

Examples of microorganisms that belong to the genus Conidiobolus include *Conidiobolus heterosporus* ATCC 12941, *Conidiobolus nanodes* CBS 183/62, *Conidiobolus lamprauges* ATCC 12585.

Examples of microorganisms that belong to the genus Yarrowia include *Yarrowia lipolytica* IFO 0746, examples of microorganisms that belong to the genus Crypthecodinium include *Crypthecodinium cohnii* ATCC 30021, 30334, 30336, 30543, 30556, 30571, 30572, 30775, 50051, 50052, 50053, 50055, 50058, and 50060, and *Thraustochytrium aureum* ATCC 2821 and 34304.

Those microorganisms are known to have ability to produce liposoluble components and accumulate significant amounts of the liposoluble component (e.g. triglycerides) in their cells. Such microorganisms may be cultured in a customary manner. No limitation is imposed on the culture medium for culturing the aforementioned microorganisms so long as it enables the microorganisms to grow well and produce the target liposoluble component. Examples of the carbon sources of the culture medium include glucose and starch, and examples of the nitrogen sources include ammonium sulfate, urea, and organic nitrogen sources such as defatted soybean flour and defatted rice bran. Metal salts such as phosphates, magnesium salts, manganese salts, and calcium salts may optionally be added to the culture medium, wherein the microorganisms are cultured while the pH and temperature of the medium are appropriately controlled.

In such a manner, microorganisms containing liposoluble components can be obtained. Since the liposoluble component is normally accumulated in microbial cells, the cells are recovered from the culture solution by way of filtration or centrifugation after the culture of microorganisms is completed.

Subsequently, the recovered cells are brought to dryness, to thereby obtain the dried microbial cells containing liposoluble components. The drying may be performed by use of a drum dryer, spray dryer, puddle dryer, or the like.

Drying according to the present invention may be performed so that the moisture content of the cells becomes 20 wt.% or less, preferably 15% or less; i.e., dryness is not necessarily completed. When the moisture content of the cells exceeds 20 wt.%, the extraction ratio decreases.

According to the present invention, the thus-obtained dried microbial cells containing liposoluble components are subjected to destruction and molding by use of an extruder, particularly a twin screw extruder. Accordingly, the dried microbial cells containing liposoluble components are pelletized as well as destructed by use of an extruder, particularly a twin screw extruder.

Use of an extruder, particularly use of a twin screw extruder, permits simultaneous mechanical destruction and pelletization of the microbial cells, resulting in shortening the steps. Moreover, destruction and molding by use of an extruder, particularly a twin screw extruder, prevents clogging of the below-described column in the step of extraction by use of the column as well as in the step of separation of the destructed cells from the extraction solvent through filtration, resulting in shortening the time required for extraction.

In the case in which there are treated microbial cells containing liposoluble components in a large amount, binders such as defatted germs may be added to the dried microbial cells so as to improve moldability into pellets.

The operational conditions (the treatment conditions) of an extruder should be appropriately selected according to the cells to be treated, and cannot be specified completely. In general, however, the treatment temperature should be about 20–120° C., the pressure about 1–100 kg/cm$^2$, and the treatment time about 1–120 seconds, preferably the treatment temperature should be about 50–120° C., the pressure about 5–100 kg/cm$^2$, and the treatment time about 5–120 seconds.

Examples of the shapes of the pallets include spherical, pseudo-spherical, and cylindrical shapes, but no particular limitation is imposed. In the case in which the pellet has a spherical shape, molding is preferably performed so that the diameter falls in the range of 1–10 mm, and particularly preferably in the range of 1–2 mm, in consideration of the permeability of a solvent. In the case in which the pellet has a shape other than spherical, pelletization is performed so that preferably the major axis of the obtained pellets falls in the range of 1.0–100 mm and the minor axis thereof falls in the range of 0.5–5 mm, and particularly preferably the major axis of the obtained pellets falls in the range of 2–50 mm and the minor axis thereof falls in the range of 1–4 mm, in consideration of the permeability of a solvent.

By performing destruction and molding in such a manner, microbial cells formed into pellets are obtained.

According to the present invention, liposoluble components contained in microbial cells is extracted (extracted and then recovered), by use of an organic solvent, from the thus-obtained microbial cells formed into pellets. Examples of the organic solvent include n-hexane, ethanol, acetone, methyl ethyl ketone, cyclohexane, diethyl ether, and ethyl acetate. Of these, n-hexane is preferred in view of the extraction ratio and application to foods.

No particular limitation is imposed on the extraction method by use of an organic solvent, but extraction by use of a packed tower (column) is preferred.

The following is an exemplary procedure for extracting and recovering liposoluble components contained in microbial cells by use of a packed column.

First, microbial cells formed into pellets (pelletized moldings) are introduced into a cylindrical packed column and an extraction solvent is allowed to flow down from the top of the packed column. Subsequently, the solvent flowing out of the bottom of the packed column is recovered, and is again allowed to flow down from the top of the packed column. This operation is repeated to perform the extraction of the liposoluble component. Allowing the solvent to reflow and be reused in such a manner can decrease the amount of solvent to be used.

The bottom of a packed column is preferably netted with wire-netting of an appropriate size or filled with a filtering aid such as diatomaceous earth or the like.

The amount of an organic solvent to be used at extraction is preferably 2–12 liters/kg of microbial cells (pelletized moldings), particularly preferably 3–5 liters/kg of microbial cells (pelletized moldings), in consideration of the extraction ratio and economical efficiency.

By removing the solvent through distillation that has flowed out of the bottom of the packed column after the sufficient extraction of the liposoluble component, the target liposoluble component contained in microbial cells can be obtained (recovered).

Removal of the solvent through distillation can be performed in a customary manner such as concentration under reduced pressure.

The thus-obtained liposoluble component contained in microbial cells may further be refined in a customary manner when necessary.

The present invention may be carried out in a manner as described above. However, microbial cells recovered from the culture solution by way of filtration or centrifugation may be destructed before being subjected to drying treatment.

Microbial cells are preferably destructed while dispersed in water. Briefly, destruction is performed while the microbial cells are dispersed and suspended in water again, or when they are dispersed or suspended in water. Use of a high-pressure homogenizer-type apparatus or the like that is employed for emulsifying or homogenizing pulverized suspension permits continuous treatments of dispersion, suspension, and destruction of cells.

EXAMPLES

The present invention will next be described in more detail by way of examples whose object is the extraction of liposoluble material contained in cells, and which should not be construed as limiting the scope of the invention. Reference Example (Measurement of the total amount of a liposoluble material contained in cells):

The following is a method of measuring the total amount of a liposoluble material contained in cells, which amount serves as the standard for calculating the extraction ratio of the liposoluble material in Examples and Comparative Examples below.

Cells of *Mucor circinelloides* HUT 1121 (deposited with Fermentation Research Institute: FERM BP-3883) were cultured in a fermentation bath under the conditions shown in Table 1, and the resultant cells containing γ-linolenic acid were recovered by filtration.

The recovered cells were dispersed in water again so that the concentration became 12%, and part of the dispersion was then subjected to dehydration by use of a double drum dryer, to thereby obtain dried cells having a moisture content of 4 wt.%.

To the thus-obtained dried cells (10 g), there were added n-hexane (100 ml) and glass beads (100 ml) having a diameter of 0.6 mm. The mixture was homogenized for 3 minutes at a rotation rate of 10,000 rpm by use of a homogenizer (Excel Auto Homogenizer DX-3; product of Nippon Seiki Co., Ltd.), and then subjected to filtration to remove glass beads and fragments of cells. Subsequently, n-hexane (100 ml) was added to the cells again, and the mixture was twice subjected to homogenization in the same manner as described above. The thus-obtained filtrate was collected and subjected to concentration under reduced pressure, to thereby obtain a yellow liposoluble material (3.6 g). This result shows that the cells contain a liposoluble material in the amount of 36%.

Example 1

Cells of *Mucor circinelloides* HUT 1121 (deposited with Fermentation Research Institute: FERM BP-3883) were cultured in a fermentation bath under the conditions shown in Table 1, and the resultant cells containing γ-linolenic acid were recovered by filtration.

The recovered cells were dispersed in water again so that the concentration became 12%, and part of the dispersion was then subjected to dehydration by use of a double drum dryer, to thereby obtain dried cells having a moisture content of 4 wt.%.

Part of the dried cells was subjected to destruction and molding by use of a twin screw extruder (TCO-75L; product of Kobe Steel, Ltd.). Molding was performed so that the pellets had a major axis of 2–50 mm and a minor axis of 1–4 mm.

The thus-pelletized cells (10 g) were charged into a glass column having an inner diameter of 20 mm as shown in FIG. 1. N-hexane (100 ml) was poured from the top of the column. After the contents were retained for 30 minutes, the stopper of the bottom was turned open to elute an n-hexane-liposoluble material mixture for collection. Then, n-hexane (100 ml) was added into the column again to collect the mixture in the same manner as described above. A liposoluble material (3.3 g) was obtained through filtration of the mixture and removal of n-hexane by distillation under reduced pressure.

The time required to elute a solvent (200 ml) from the column (solvent elution time) was measured. The solvent elution time and extraction ratio of the liposoluble material are shown in Table 2.

Comparative Example 1

The procedure of Example 1 was performed, except that destruction and molding by use of a twin screw extruder were omitted. The results are shown in Table 2.

Comparison of the results of Example 1 and those of Comparative Example 1 demonstrates the following.

In Example 1, the solvent elution time was as short as 6 minutes and the extraction ratio was as high as 94%, whereas in Comparative Example 1 in which destruction and molding by use of a twin screw extruder were not conducted but the procedure was otherwise carried out under the same conditions as those of Example 1, the solvent elution time was prolonged to 16 minutes and the extraction ratio was only 42%.

The results prove that destruction and molding of cells by use of a twin screw extruder remarkably increase permeability of a solvent to the cells and the extraction efficiency.

Example 2

Cells of *Mucor circinelloides* HUT 1121 (deposited with Fermentation Research Institute: FERM BP-3883) were cultured in a fermentation bath under the conditions shown in Table 1, and the resultant cells containing γ-linolenic acid were recovered by filtration.

The recovered cells were dispersed in water again so that the concentration became 12%, to thereby obtain a suspension of the cells.

The suspension was subjected to destruction at 700 kg/cm$^2$ and a flow rate of 60 liters/hour by use of a high-pressure homogenizer (HV-OH-0.7–3.7S; product of Izumi Food Machinery, Co.). The destructed cells were dehydrated by use of a double drum drier to thereby obtain dried cells having a moisture content of 4 wt.%.

The dried cells were subjected to the procedure of Example 1, i.e., destruction and molding and extraction of a liposoluble material, to thereby obtain a liposoluble material (3.4 g). The results are shown in Table 2.

Comparative Example 2

The procedure of Example 2 was repeated, except that destruction and molding by use of a twin screw extruder were omitted. The results are shown in Table 2.

Comparison of the results of Example 2 and those of Comparative Example 2 demonstrates the following.

In Comparative Example 2 in which destruction and molding were omitted, the extraction ratio was satisfactory at 90%, but the solvent elution time was as long as 38 minutes. This indicates that the column was clogged with cells that had been finely destructed through homogenization.

In contrast, in Example 2 in which destruction and molding were conducted, the solvent elution time was as short as 7 minutes and the extraction ratio was as high as 96%. Therefore, cells which were pelletized in Example 2 did not cause clogging of the column and the solvent effectively flowed down through the column.

The results prove that permeability of a solvent to the cells increases and the extraction efficiency remarkably increases through destruction and molding by use of a twin screw extruder after homogenization.

Example 3

The procedure of Example 1 was performed, except that *Mortierella ramaniana var. angrispora* IFO 8187 was used and cultured under the conditions shown in Table 1 instead of *Mucor circinelloides* HUT 1121 (deposited with Fermentation Research Institute: FERM BP-3883). The results are shown in Table 2.

As shown in Table 2, in Example 3, the solvent elution time was 8 minutes and the extraction ratio was as high as 94%. These values are approximately the same as those of Example 1.

The results prove that a liposoluble material contained in cells is effectively extracted, in a procedure in which *Mortierella ramaniana var. angrispora* IFO 8187 is used as the cells.

Comparative Example 3

The procedure of Example 3 was performed, except that destruction and molding by use of a twin screw extruder were omitted. The results are shown in Table 2.

Comparison of the results of Example 3 and those of Comparative Example 3 demonstrates the following.

In Comparative Example 3 in which destruction and molding by use of a twin screw extruder were not conducted but in which the procedure was otherwise carried out under the same conditions as those of Example 3, the solvent elution time was prolonged to 21 minutes and the extraction ratio was only 37%.

The results prove that permeability of a solvent to the cells increases and the extraction efficiency remarkably increases through destruction and molding of the cells by use of a twin screw extruder, in a procedure in which *Mortierella ramaniana var. angrispora* IFO 8187 is used as the cells.

Example 4

The procedure of Example 1 was performed, except that *Conidiobolus nanodes* CBS 183/62 was used and cultured under the conditions shown in Table 1 instead of *Mucor circinelloides* HUT 1121 (deposited with Fermentation Research Institute: FERM BP-3883). The results are shown in Table 2.

As shown in Table 2, in Example 4, the solvent elution time was 7 minutes and the extraction ratio was as high as 92%. These values are approximately the same as those of Example 1.

The results prove that a liposoluble material contained in cells is effectively extracted as in the case of Example 1, in which *Conidiobolus nanodes* CBS 183/62 is used as the cells.

Comparative Example 4

The procedure of Example 4 was performed, except that destruction and molding by use of a twin screw extruder were omitted. The results are shown in Table 2.

Comparison of the results of Example 4 and those of Comparative Example 4 demonstrates the following.

In Comparative Example 4 in which destruction and molding by use of a twin screw extruder were not conducted but in which the procedure was otherwise carried out under the same conditions as those of Example 4, the solvent elution time was prolonged to 19 minutes and the extraction ratio was only 39%.

The results prove that permeability of a solvent to the cells increases and the extraction efficiency remarkably increases through destruction and molding of the cells by use of a twin screw extruder, in a procedure in which *Conidiobolus nanodes* CBS 183/62 is used as the cells.

Example 5

The procedure of Example 1 was performed, except that *Yarrowia lipolytica* IFO 0746 was used and cultured under the conditions shown in Table 1 instead of *Mucor circinelloides* HUT 1121 (deposited with Fermentation Research Institute: FERM BP-3883). The results are shown in Table 2.

As shown in Table 2, in Example 5, the solvent elution time was 8 minutes and the extraction ratio was as high as 92%. These values are approximately the same as those of Example 1.

The results prove that a liposoluble material contained in cells is effectively extracted as in the case of Example 1, in which *Yarrowia lipolytica* IFO 0746 is used as the cells.

Comparative Example 5

The procedure of Example 5 was performed, except that destruction and molding by use of a twin screw extruder were omitted. The results are shown in Table 2.

Comparison of the results of Example 5 and those of Comparative Example 5 demonstrates the following.

In Comparative Example 5 in which destruction and molding by use of a twin screw extruder were not conducted but in which the procedure was otherwise carried out under the same conditions as those of Example 5, the solvent elution time was prolonged to 26 minutes and the extraction ratio was only 28%.

The results prove that permeability of a solvent to the cells increases and the extraction efficiency remarkably increases through destruction and molding of the cells by use of a twin screw extruder, in a procedure in which *Yarrowia lipolytica* IFO 0746 is used as the cells.

TABLE 1

| | Lipid-producing substances | | | |
|---|---|---|---|---|
| | *Mucar circinelloides* | *Mortierella Ramaniana* Var. *angrispora* | *Conidiobolus nanodes* | *Yarrowia Lipolytica* |
| Medium composition | | | | |
| Glucose | 250 g/l | 200 g/l | 150 g/l | 40 g/l |
| Ammonium sulfate | 16.5 g/l | 16.5 g/l | — | 3 g/l |
| Mono-potassium phosphate | 9 g/l | 9 g/l | 1.5 g/l | 3 g/l |
| $MgSO_4.7H_2O$ | 1 g/l | 1 g/l | 0.5 g/l | 0.5 g/l |
| Yeast extract | 0.6 g/l | 0.6 g/l | 15 g/l | 0.6 g/l |
| Polypeptone | — | 0.6 g/l | 30 g/l | 0.6 g/l |
| Minor metal sol. | 8 ml/l | 6 ml/l | 1 ml/l | 1 ml/l |
| Culture conditions | | | | |
| Temperature | 30° C. | 30° C. | 30° C. | 30° C. |
| PH | 5 adjusted with NaOH | 3.5 adjusted with NaOH | free | 5 adjusted with NaOH |

*Minor metal sol.:
$FeSO_4.7H_2O$ 5 g/l,
$CaCl_2.2H_2O$ 0.6 g/l,
$ZnSO_4.7H_2O$ 0.5 g/l,
$MnCl_2.4H_2O$ 0.5 g/l,
$CuSO_4.5H_2O$ 0.1 g/l,
Deionized water 1 liter

TABLE 2

| | | Twin Extruder Treatment | Elusion Time (min) | Extraction Ratio (%) |
|---|---|---|---|---|
| Ex. 1 | *Mucor circinelloides* HUT 1121 | Yes | 6 | 94 |
| Comp. Ex. 1 | *Mucor circinelloides* HUT 1121 | No | 16 | 42 |
| Ex. 2 | *Mucor circinelloides* HUT 1121 | Yes, + High pressure homogenizing treatment | 7 | 96 |
| Comp. Ex. 2 | *Mucor circinelloides* HUT 1121 | No, High pressure homogenizing treatment alone | 38 | 90 |
| Ex. 3 | *Mortierella ramaniana var. angrispora* IFO 8187 | Yes | 8 | 94 |
| Comp. Ex. 3 | *Mortierella ramaniana var. angrispora* IFO 8187 | No | 21 | 37 |
| Ex. 4 | *Conidiobolus nanodes* CBS 183/62 | Yes | 7 | 92 |
| Comp. Ex. 4 | *Conidiobolus nanodes* CBS 183/62 | No | 19 | 39 |
| Ex. 5 | *Yarrowia lipolytica* IFO 0746 | Yes | 8 | 92 |
| Comp. Ex. 5 | *Yarrowia lipolytica* IFO 0746 | No | 26 | 28 |

Example 6

Water was added to dried cells of *Mucor circinelloides* HUT 1121 (deposited with Fermentation Research Institute: FERM BP-3883) having a moisture content of 4 wt.%, obtained at Example 1, to there by produce cell samples having moisture contents of 10 wt. %, 15 wt. %, 20 wt. %, 25 wt. %, and 30 wt. %, respectively.

Each of the cell samples was subjected to destruction and molding and extraction of a liposoluble material under the same conditions as those of Example 1. The extraction ratios of these cell samples are shown in Table 3.

TABLE 3

| | Liposoluble material-producing material | Moisture content of cells (%) | Solvent elution time | Extraction ratio (%) |
|---|---|---|---|---|
| Example 6 | *Mucor circinelloides* HUT 1121 | 4 | 6 | 94 |
| | | 10 | 6 | 95 |
| | | 15 | 6 | 92 |
| | | 20 | 7 | 87 |
| | | 25 | 6 | 65 |
| | | 30 | 6 | 61 |

The results of Example 6 shown in Table 3 demonstrate the following.

The solvent elution times of cell samples having moisture contents of 4 wt. %, 10 wt. %, 15 wt. %, and 20 wt. % were 6 minutes, 6 minutes, 6 minutes, and 7 minutes, respectively, and the extraction ratios were 94%, 95%, 92%, and 87%, respectively. The results prove that a liposoluble material contained in the cells is effectively extracted.

In contrast, the solvent elution times of cell samples having moisture contents of 25 wt. % and 30 wt. % were 6 minutes in both cases and the extraction ratios were as low as 65% and 61%, respectively.

The results prove that the moisture content of the cells must be 20 wt. % or less in order to increase efficiency in extraction of a liposoluble material contained in the cells.

As described above, according to the present invention, dried microbial cells are not finely destructed, but are subjected to destruction and molding into pellets by use of a twin screw extruder. Therefore, there may be prevented clogging of a column in the step of extraction by use of the column as well as the step of separation of the destructed cells from the extraction solvent through filtration, thereby shortening the time required for extraction.

Also in the present invention, use of an extruder, particularly use of a twin screw extruder, permits simultaneous mechanical destruction and pelletization of the microbial cells, which results in simplifying the steps.

Moreover, according to the present invention, liposoluble components contained in microbial cells may effectively be extracted and recovered by use of a small amount of solvent and through safe operations.

What is claimed is:

1. A method of extracting liposoluble components contained in microbial cells which contain liposoluble components, comprising drying microbial cells containing liposoluble components, simultaneous disrupting and molding of the dried microbial cells into pellets by use of an extruder, and extracting the contained liposoluble component by use of an organic solvent.

2. The method according to claim 1, wherein the extruder is a twin screw extruder.

3. The method according to claim 1, wherein the moisture content of the dried microbial cells is not more than 20% by weight.

* * * * *